United States Patent [19]
Sodhi et al.

[11] Patent Number: 6,096,035
[45] Date of Patent: Aug. 1, 2000

[54] MULTIPOLAR TRANSMURAL PROBE

[76] Inventors: Chris Sodhi, 3 Lawson Street, Sans Soxei, New South Wales 2226; Michael Daly, 25 Darvall Road, Eastwood, New South Wales 2122; David Ross, 41 Cheltenham Road, Cheltenham, New South Wales 2199; Pramesh Kovoor, 21/1 Reid Avenue, Wentworthville, New South 2145; Ilija Koevski, 56 Portico Parade Toongabbie, New South Wales 2146, Wales, all of Australia

[21] Appl. No.: 09/031,861

[22] Filed: Feb. 27, 1998

[51] Int. Cl.⁷ .................................................. A61B 17/36
[52] U.S. Cl. ........................ 606/41; 607/101; 607/102; 600/374
[58] Field of Search .................. 606/31, 41, 42, 606/45, 48–50; 600/374; 607/100–102

[56] References Cited

U.S. PATENT DOCUMENTS

| | | |
|---|---|---|
| 4,966,597 | 10/1990 | Cosman . |
| 5,472,441 | 12/1995 | Edwards et al. ........................... 606/41 |
| 5,599,345 | 2/1997 | Edwards et al. ........................... 606/41 |
| 5,688,266 | 11/1997 | Edwards et al. ........................... 606/31 |
| 5,849,028 | 12/1998 | Chen ........................................ 607/102 |
| 5,855,552 | 1/1999 | Houser et al. ........................... 600/374 |

FOREIGN PATENT DOCUMENTS

| | | |
|---|---|---|
| 9520475/95 | 6/1995 | Australia . |
| 0049780 | 9/1981 | European Pat. Off. . |
| PCT/US92/ 04315 | 5/1992 | WIPO . |
| PCT/US94/ 13932 | 12/1994 | WIPO . |
| PCT/US95/ 13129 | 10/1995 | WIPO . |

*Primary Examiner*—Michael Peffley
*Attorney, Agent, or Firm*—Knobbe, Martens, Olson & Bear, LLP

[57] ABSTRACT

The present invention relates to a needle-like probe (1) for use in electrical potential sensing and RF ablation of tissue, a method of making such probes (1), and a probe array comprising a number of such probes (1). The probe (1) has an elongated body (2, 22) with one end (9, 29) adapted for penetration of tissue. The body (2, 22) has sufficient rigidity to be inserted into the tissue. The elongated body (2, 22) also comprises two or more electrodes (7, 27) separated and spaced apart from each other along the elongated body (2, 22) by insulative material (8, 28). Each electrode (7, 27) has at least one electrical conductor (10, 11) coupled to the electrode (7, 27). The electrode (7, 27) is capable of delivering RF energy to the tissue surrounding the electrode (7, 27) and sensing the electrical potential of the tissue. Preferably, the two or more electrodes (7, 27) each comprises a metal band incorporated in the elongated body (2, 22) and optionally include a thermal sensing means for measuring the temperature at the interface between the electrode (7, 27) and the tissue. Still further, the elongated body (2, 22) can internally incorporate an elongated rigid member (14) for providing structural stiffening of the probe (1). The elongated rigid member (14) can be comprised of metal and is rigidly fixed to at least the one end (9,29) adapted for penetration of the tissue. Preferably, the two or more electrodes (7, 27) and the insulative material (8, 28) form a tubular structure and the interior cavity of the tubular structure is filled with matrix material (16). Preferably, the probe (1) comprises at least four electrodes (7, 27) and at least three insulative portions (8, 28) interleaved therewith. Optionally, the elongated body (2, 22) has a substantially arcuate or curved form.

15 Claims, 4 Drawing Sheets

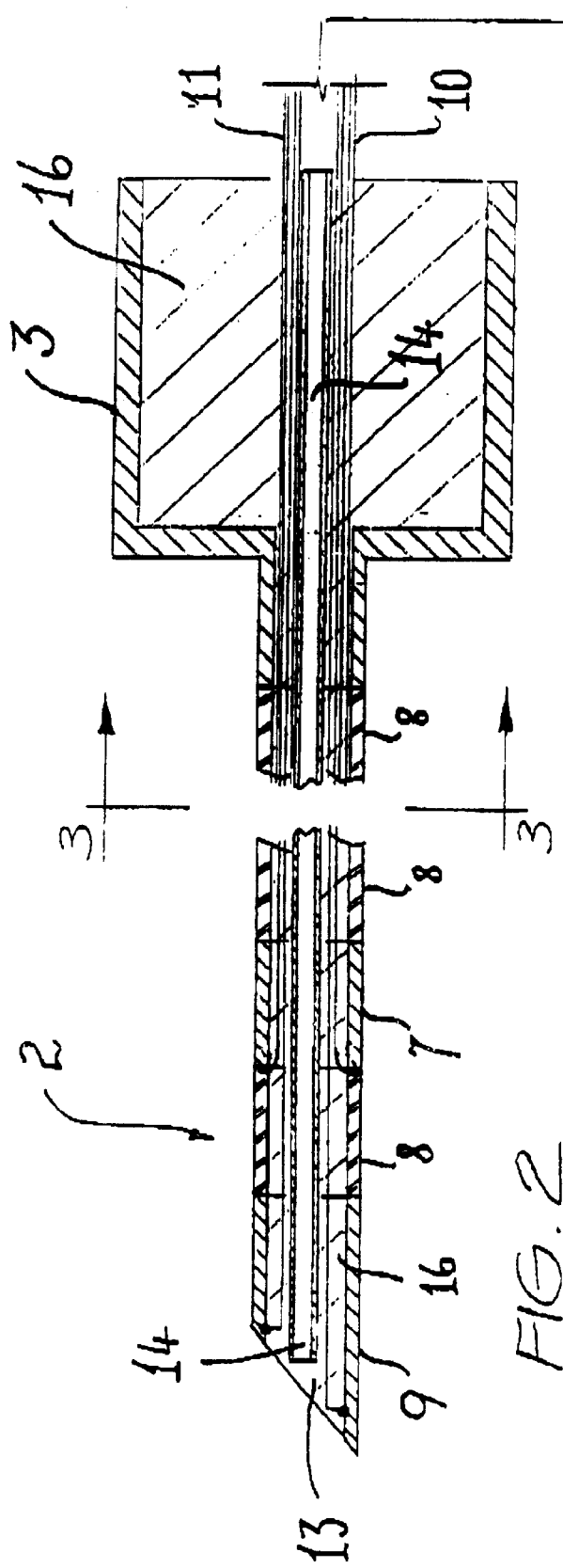
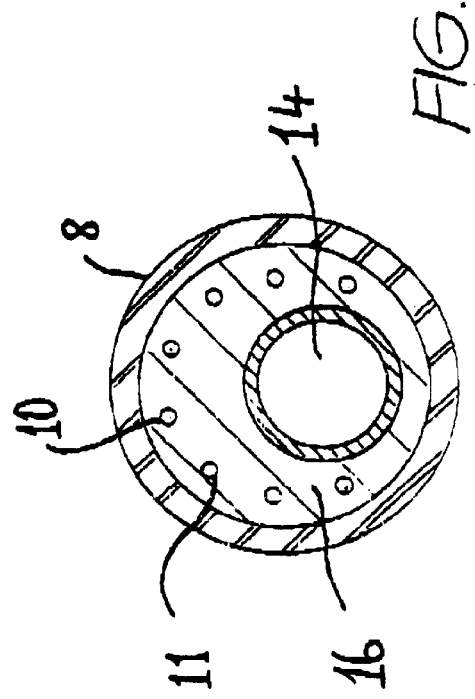
FIG. 2
FIG. 3

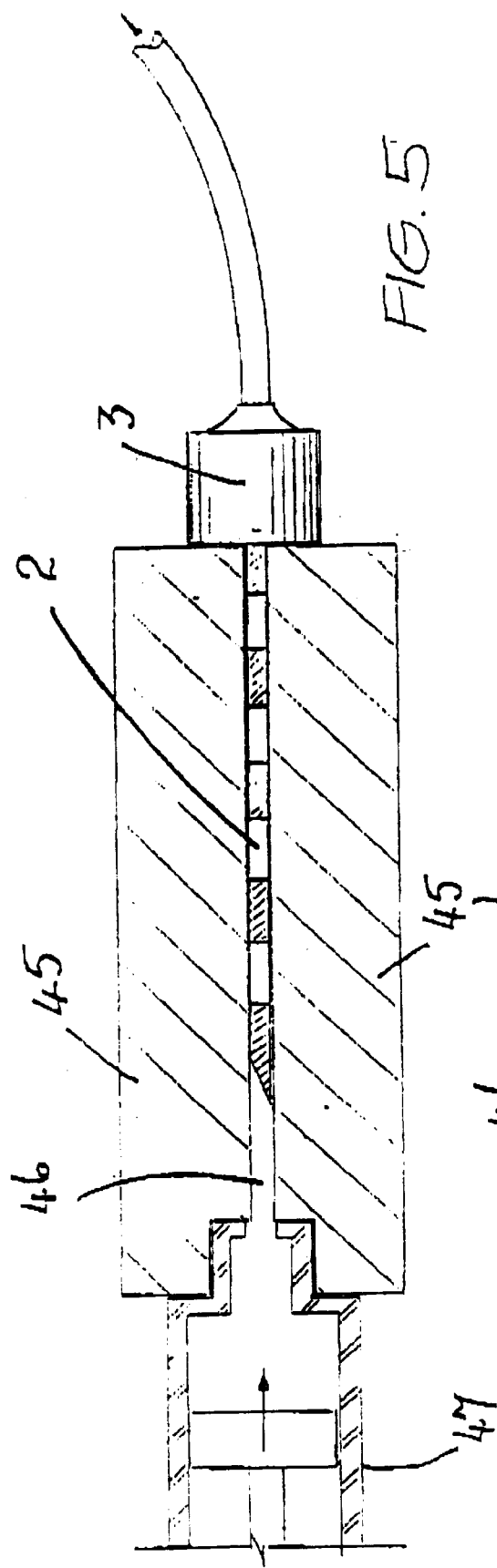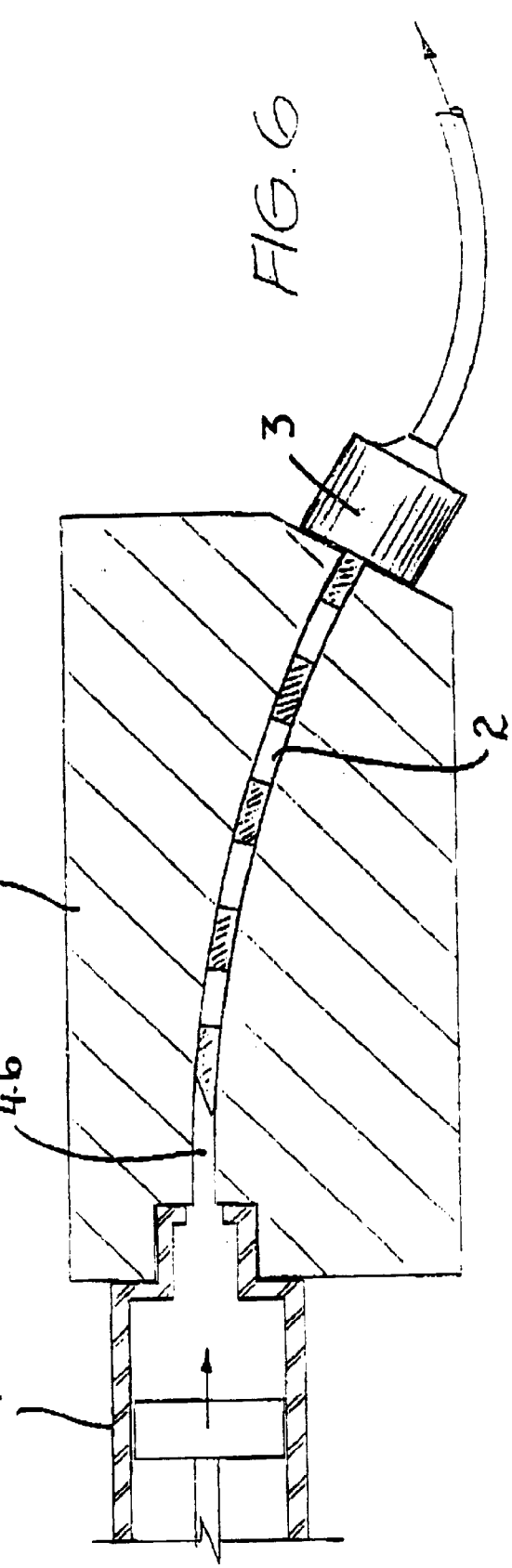

MULTIPOLAR TRANSMURAL PROBE

BACKGROUND

The present invention generally relates to the sensing of electrical potentials in tissue and to the radio frequency (RF) ablation of tissue, and in particular to probes for doing so and methods of constructing such probes.

It is known that damaged heart muscles can cause abnormal activities of the electrical signals that are generated to create muscle contraction. As a result of this damaged tissue, the heart instead of beating as "normal" can have an increased heartbeat (ventricular tachycardia).

Hitherto, such cardiac defects have been treated either by means of drugs or by means of a catheter inserted into the heart via a patient's blood passages (e.g., a vein). With drug treatment, the effects are not entirely predictable and often many side effects occur. In general, the treatment with drugs is thought to be only approximately 30 to 35% successful.

The second treatment involves the insertion of electrodes into the heart via a catheter inserted through a vein. Such a catheter is typically an elongated, cylindrical body made of flexible material that is fitted with two or more electrodes at a distal end. Radio frequency energy is then applied between two electrodes so as to cause ablation. In particular, it is desired, in this way, to remove the defective tissue, or at least change its electrical properties, to prevent re-entry of the electrical signals necessary to cause contraction of the muscle. It has been found difficult to locate correctly the catheter and the necessary electrodes with any precision, partly due to the interior nature of the mechanism of the arrhythmia and also due to the continuous movement of the heart muscles.

SUMMARY OF THE INVENTION

It is therefore an object of the present invention to both provide probes and a method of manufacturing same to overcome one or more disadvantages of the prior art.

In accordance with a first aspect of the invention, there is provided a needle-like probe for use in electrical potential sensing and RF ablation of tissue, comprising: an elongated body with one end adapted for penetration of tissue and having sufficient rigidity to be inserted into the tissue, the elongated body comprising two or more electrodes separated and spaced apart from each other along the elongated body by insulative material; each electrode having at least one electrical conductor coupled to the electrode, the electrode capable of delivering RF energy to the tissue surrounding the electrode and sensing the electrical potential of the tissue.

Preferably, the two or more electrodes each comprise a metal band incorporated in the elongated body and optionally include a thermal sensing means for measuring the temperature at the interface between the electrode and the tissue. Still further, the elongated body can internally incorporate an elongated rigid member for providing structural stiffening of the probe. The elongated rigid member can be comprised of metal and is rigidly fixed to at least the one end adapted for penetration of the tissue.

Preferably, the two or more electrodes and the insulative material form a tubular structure and the interior cavity of the tubular structure is filled with matrix material.

Preferably, the probe comprises at least four electrodes and at least three insulative portions interleaved therewith. Optionally, the elongated body has a substantially arcuate or curved form.

In accordance with a second aspect of the present invention, there is disclosed a multipolar transmural probe, the probe comprising a needle shaped shank extending from a head, the shank being formed from a plurality of substantially tubular conductive portions, each adjacent pair of which has a substantially tubular insulative member interposed therebetween with the hollow interiors of the portion and members being aligned to form a passageway leading to the head, electrical conductors extending through the passageway to provide an electrically conductive path between each the portion and the head, and stiffening means extending through the passageway and being in force transmitting relationship with the portions and members.

Preferably, the probe includes at least one thermocouple associated with a corresponding pair of the conductive portions.

Preferably, the stiffening means comprises a solid steel needle embedded in a flowable, hardenable material (such as epoxy resin) which fills the interior of the passageway not occupied by the stiffening needle and electrical conductors.

In accordance with a third aspect of the present invention, there is provided a method of manufacturing a multipolar transmural probe, the method comprising the steps of:

(i) electrically connecting each of a plurality of substantially tubular conductive portions with a corresponding electrical conductor, (ii) threading the conductive portions onto a stiffening needle to form a passageway with a substantially tubular insulative member located on the needle between each adjacent pair of conductive portions with the electrical conductors passing through the passageway, (iv) clamping the portions and members to retain same in substantially longitudinal axial compression to immobilise same, and (v) forcing a flowable hardenable substance into the passageway.

In accordance with a fourth aspect of the invention, there is provided a probe array for use in electrical potential sensing and RF ablation of tissue, the array comprising a plurality of needle-like probes, wherein each of the needle-like probes comprises: an elongated shank with one end adapted for piercing tissue and having sufficient rigidity to be inserted into the tissue, the shank comprising two or more electrodes displaced from each other along the shank by insulative material; each electrode having at least one electrical conductor coupled to the electrode, the electrode capable of delivering RF energy to the tissue surrounding the electrode and sensing the electrical potential of the tissue.

Preferably, the two or more electrodes each comprise a metal band forming part of the elongated shank and optionally include a thermocouple for measuring the temperature at the interface between the electrode and the tissue.

Preferably, the two or more electrodes and corresponding insulative sections form a tubular structure through which the at least one electrical conductor of each electrode passes in each probe of the array. Further, the elongated rigid member of each probe is optionally comprised of metal and is rigidly fixed to at least the one end adapted for piercing the tissue. Still further, the interior cavity of the tubular structure is filled with matrix material.

BRIEF DESCRIPTION OF THE DRAWINGS

Embodiments of the present invention will now be described with reference to the drawings in which:

FIG. 2 is a truncated longitudinal cross-section through the shank and head of the probe of FIG. 1, FIG. 3 is a transverse cross-sectional view taken along the line 3—3 of FIG 2, FIG. 5 is a cross-sectional view through a clamp and syringe used in the manufacture of the probe of either FIGS. 2 or 4, and FIG. 6 is a view similar to FIG. 5 but illustrating the manufacture of a third embodiment having a curved shank.

DETAILED DESCRIPTION

The present invention is concerned with a different solution to those proposed using a catheter that passes through a passageway (e.g. a vein) of the patient and hence into the heart. Instead, open-chest surgery (thoracotomy) is undertaken and electrodes are able to be inserted directly into the myocardium, or heart muscle, from the exterior of the heart. The electrical probes can be used to detect muscle that creates irregular heartbeats (arrhythmia). Upwards of approximately 30 to 70 of such probes, each having one or more electrodes, can be required. Other numbers of probes (and likewise electrodes) can be used without departing from the scope and spirit of the invention.

If the electrical potentials experienced by the electrodes of such probes are measured, an algorithm can be applied to the detected electrical signals that enables detection of those muscles creating the arrhythmia. Once those muscles have been detected, the application of RF energy to electrodes straddling the muscle can be used to disable the defective tissue. For this procedure to be carried out, it is necessary to have a needle-like probe that is able to be inserted into the myocardium and which are preferably both detect the small electrical potentials generated by the patient to contract the muscle, and also deliver the RF energy. While the embodiments of the invention are described with reference to heart muscle (myocardium), it will be apparent to a person skilled in the art that the present invention has broader application to other types of tissue without departing from the scope and spirit of the invention.

During ablation, it is desirable to closely regulate the amount of heart muscle destroyed. Monitoring of the temperature at the interface between the electrode and the heart muscle and adjusting the amount of radio frequency energy delivery has been found to be the best way of doing this. By incorporation of one or more thermocouples within the electrodes of the probes, such monitoring becomes possible. Alternatively, a thermistor of other temperature sensing transducer can be employed in each electrode to measure the temperature. A similar problem arises in the field of neurophysiology and the arrangements of the present invention find application in the RF ablation of tumours, or other abnormalities, of the invention. The embodiments of the invention will now be described in detail with reference to FIGS. 1 to 6.

Figure 1:
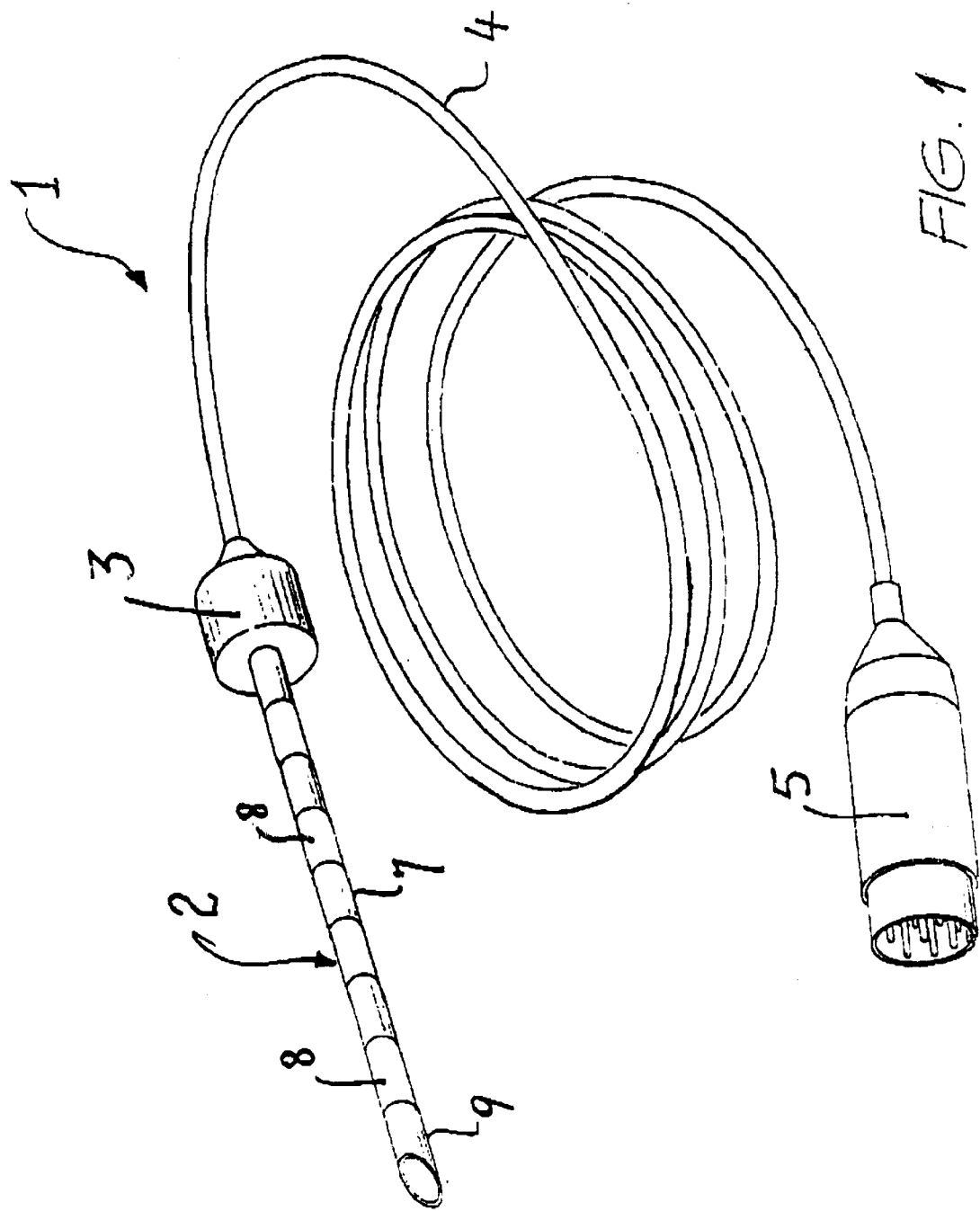
FIG. 1 is a schematic perspective view of the entire probe of the first embodiment.

As seen in FIG. 1, the probe 1 takes the form of a shank 2 which extends from a head 3 that is connected by means of a cable 4 to an electrical connector 5. The electrical connector 5 of FIG. 1 is illustrated as a cylindrically shaped, socket connector with a number of pins projecting within the inner metal sleeve of the connector 5. It will be apparent to a person skilled in the art that other types of connectors having different configurations can be practiced without departing from the scope and spirit of the invention. The shank 2 is formed from a series of conductive portions 7 which are separated by coaxially aligned insulative members 8. Both the portions 7 and members 8 are tubular, and thus the shank 2 has a hollow interior. A piercing member 9 at the distal end of the shank 2 is adapted for penetration of tissue. Preferably, the member 9 is made of metal and has a bevelled edge for penetrating or piercing tissue. Optionally, the member 9 can be used as an electrode and may have a thermocouple. It will be apparent to a person skilled in the art that modifications to the member 9 and/or the shank 2 can be made without departing from the scope and spirit of the invention. The piercing member 9 may also be separated from a portion 7 by an insulative member 8.

As best seen in FIG. 2, each of the conductive portions 7 preferably has two separate insulated electrical conductors spot welded thereto. One of these conductors 10 is used to provide electrical connection to the conductive portion itself whilst the other conductor 11 is used in the creation of a thermocouple. Thus, whilst the wire 10 is preferably formed from stainless steel and is welded to the stainless steel conductive portion 7, the other wire 11 is formed from a material such as nickel. The thermocouple wires 11 enable the temperature of the myocardium to be measured.

The hollow interiors of the portions 7, members 8, and piercing member 9 constitute a passageway 13 within which is located a TEFLON (trademark) coated stainless steel needle 14 which considerably stiffens the shank 2. A like, suitably stiff, elongated object may also be used instead of a stainless steel needle. The members 8 are preferably fabricated from TEFLON. As best illustrated in FIG. 3, the needle 14 and wires 10, 11 are set in a matrix 16 formed from a flowable, hardenable substance such as epoxy resin, or the like. Thus, all the materials used are preferably biocompatible.

With reference to FIG. 3, the preferred dimensions for the shank 2 are as follows:

Outer diameter: 0.8 mm,

Inner diameter of portion 7 and members 8: 0.66 mm,

Length of portions 7 and members 8: 1.5 mm,

Outer diameter of needle 14: 0.35 mm.

In an alternative embodiment, the length of the portions 7 and members 8 is increased to 3.0 mm. It is also not necessary for the portions 7 and members 8 to each be the same length. The piercing member 9 can have substantially the same dimensions as that of portion 7 and member 8. However, it will be apparent to a person skilled in the art that modifications can be made to the piercing member 9 without departing from the scope and spirit of the invention.

In yet another embodiment being a septal probe, the shank has the following dimensions:

Outer diameter: 1.1 mm,

Inner diameter of portion 7 and member 8: 0.9 mm,

Length of portion 7: 2.0 mm,

Length of member 8: 2.5 mm,

Outer diameter of needle 14: 0.4 mm.

It will be apparent to a person skilled in the art that changes can be made to the dimensions of the probe and its components without departing from the scope and spirit of the invention. Further, the number of electrodes and the dimensions of the electrodes can be programmed, or varied, to suit particular applications. Likewise, the overall structure of the needle-like probe can be programmed including variations to the dimensions of the insulative material. Thus, for example, the overall length of the shank 2 can be doubled to provide twice as many electrodes as set forth above in the preferred embodiment.

Figure 4:
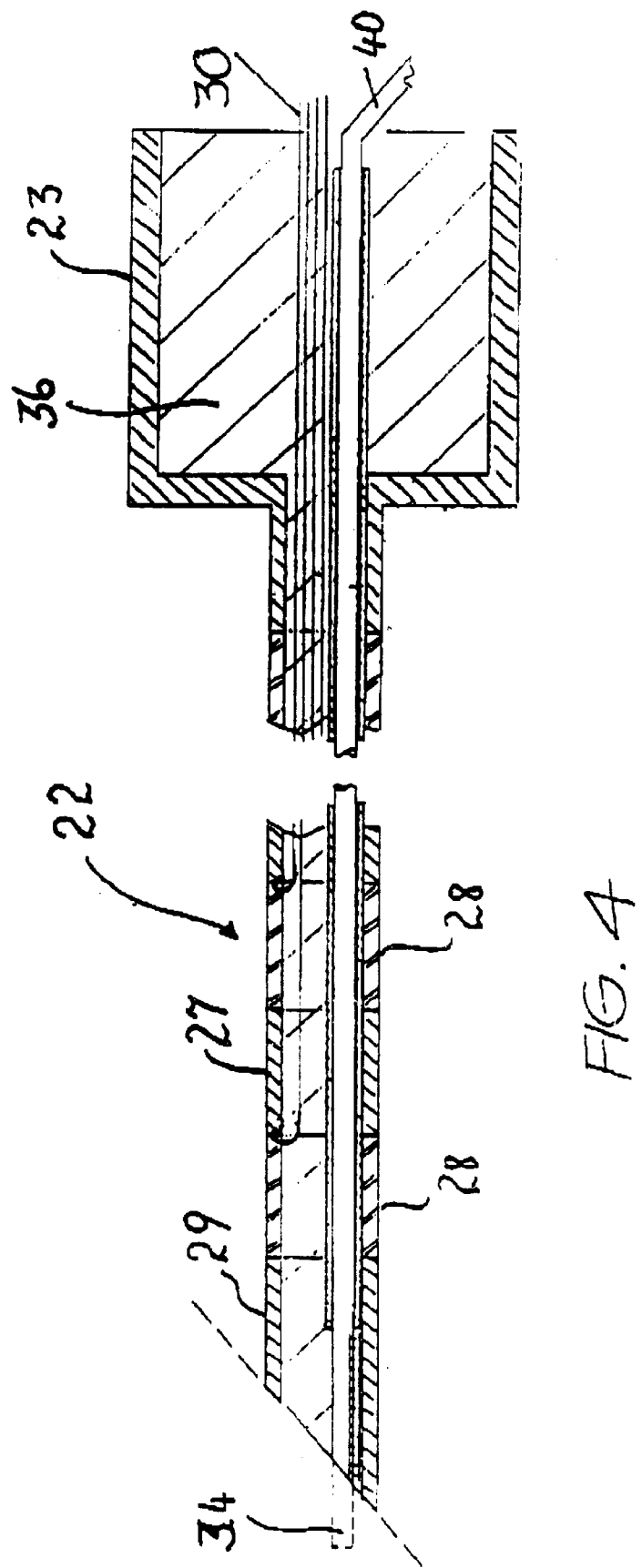
FIG. 4 is a view similar to FIG. 2 but illustrating the probe of the second embodiment.

FIG. 4 illustrates an alternative arrangement in which all reference numerals for like elements are increased by twenty (20). The shank 22 and head 23 are essentially as before. Only conductive wire 30 are provided and the needle 34 is provided with a kink 40 within the head 23 to provide a stronger anchor. In addition, the leading end of the needle 34 has its TEFLON coating stripped away and is electrically resistance welded to the leading conductive portion 29, which is adapted to penetrate tissue. As indicated by means of broken lines in FIG. 4, this welding step takes place preferably prior to the trimming or cutting of the leading conductive portion 29 which is thereby sharpened in order to provide a sharp point to the shank 22. The above description of piercing member 9 applies equally to leading conductive portion or piercing member 29.

After assembly of the portions 7, members 8, piercing member 9, wires 10, 11 and needle 14, the entire shank 2 is placed within a clamp 45 as seen in FIG. 5, which has an opening 46 which corresponds to the external dimensions of the shank 2. This opening 46 is aligned with a syringe 47 which is used to inject the matrix material under pressure into the passage 13. The matrix material 16 fills not only the passage 16 but also the hollow interior of the head 3. The issuing of matrix material from the head 3 is an indication that the entire passage 13 is filled and therefore the action of the syringe can be terminated. These steps may be modified to suit individual requirements without departing from the scope and spirit of the invention.

FIG. 6 illustrates an alternative embodiment where the shank 2 is arcuate or curved and, preferably is curved in such a way as to follow the contours of the heart muscles.

The probes are utilised by opening the chest wall of the patient, the inserting numbers of the probe shanks 2 into the heart muscle. The voltages appearing at the portions 7 (and optionally piercing member 9) are then able to be measured via the connector 5. This enables a determination to be made as to the location of defective tissue. RF energy is then able to be applied between either the portions 7 of a probe shank 2, or one or more portions 7 of two or more different shanks 2, or between portions 7 of one or more probes and an external electrode applied to the surface of the body in order to ablate or otherwise change the electrical characteristics of the defective tissue. Alternatively, this may be done utilising the piercing member 9 if configured as an electrode. The thermocouple wires 11 preferably enable the heat thereby generated to be measured or estimated. Also repeated application of RF energy to the electrode can, if necessary, be made with temperature and electrical potential measurements being made between the applications of RF energy.

It will be apparent to a person skilled in the art that modifications to the structure and construction of the probe can be practiced without departing from the scope and spirit of the invention. For example, the needle structure could be made using lithographic techniques in combination with sputtering and deposition techniques to build the needle-like probes in a layer-by-layer process.

The foregoing describes only some embodiments of the present invention and modifications, obvious to those skilled in the art, can be made thereto without departing from the scope of the present invention. For example, although the above description is made with reference to humans, the present invention is equally applicable to other mammals such as racehorses or other applications in industrial environments.

We claim:

1. A needle-like probe for use in electrical potential sensing and RF ablation of tissue, comprising:

an elongated body with one end adapted for penetration of tissue and having sufficient rigidity to be inserted into said tissue, said elongated body comprising two or more electrodes separated and spaced apart from each other along said elongated body by insulative material;

each electrode having at least one electrical conductor coupled to said electrode, said electrode capable of delivering RF energy to said tissue surrounding said electrode and sensing said electrical potential of said tissue, wherein said two or more electrodes and said insulative material from a tubular structure and the interior cavity of said tubular structure is filled with matrix material.

2. The probe according to claim 1, wherein said two or more electrodes each comprise a metal band incorporated in said elongated body.

3. The probe according to claim 2, wherein each electrode comprises a thermal sensing means for measuring the temperature at the interface between said electrode and said tissue.

4. The probe according to claim 1, wherein said elongated body internally incorporates an elongated rigid member for providing structural stiffening of said probe.

5. The probe according to claim 4, wherein said elongated rigid member is comprised of metal or suitably rigid material and is rigidly fixed to at least said one end adapted for penetration of said tissue.

6. The probe according to claim 1 wherein said probe comprises at least four electrodes and at least three insulative portions interleaved therewith.

7. The probe according to claim 1 wherein said elongated body has a substantially arcuate or curved form.

8. A multiport transmural probe, said probe comprising:

a needle shaped shank extending from a head, said shank being formed from a plurality of substantially tubular conductive portions, each adjacent pair of which has a substantially tubular insulative member interposed therebetween with hollow interiors of said portion and members being aligned to form a passageway leading to said head, electrical conductors extending through said passageway to provide an electrically conductive path between each said portion and said head, and stiffening means extending through said passageway and being in force transmitting relationship with said portions and members, wherein the stiffening means comprises a solid steel needle embedded in a flowable hardenable material which fills the interior of the passageway not occupied by the stiffening needle and electrical conductors.

9. The probe according to claim 8 further comprising at least one thermocouple associated with a corresponding pair of said conductive portions.

10. The probe according to claim 8 wherein the flowable, hardenable material comprises an epoxy resin.

11. A method of manufacturing a multipolar transmural probe, said method comprising the steps of:

electrically connecting each of a plurality of substantially tubular conductive portions with a corresponding electrical conductor;

threading the conductive portions onto a stiffening needle to form a passageway with a substantially tubular insulative member located on said needle between each adjacent pair of conductive portions with said electrical conductors passing through said passageway;

clamping said portions and members to retain same in substantially longitudinal axial compression to immobilise same; and forcing a flowable hardenable substance into said passageway.

12. A probe array for use in electrical potential sensing an RF ablation of tissue, said array comprising a plurality of needle-like probes, wherein each of said needle-like probes comprises:
   an elongated shank with one end adapted for piercing tissue and having sufficient rigidity to be inserted into said tissue, said shank comprising tow or more electrodes displaced from each other along said shank by insulative material;
   each electrode having at least one electrical conductor coupled to said electrode, said electrode capable of delivering RF energy to said tissue surrounding said electrode and sensing said electrical potential of said tissue, wherein said two or more electrodes and corresponding insulative sections form a tubular structure through which said at lest one electrical conductor of each electrode passes, wherein the interior cavity of said tubular structure is filled with matrix material.

13. The probe array according to claim 12, wherein said two or more electrodes each comprise a metal band forming part of said elongated shank.

14. The probe array according to claim 13, wherein each electrode comprises means for measuring the temperature at the interface between said electrode and said tissue.

15. The probe array according to claim 12, wherein said elongated shank internally incorporates an elongated rigid member, said elongated rigid member being comprised of metal and is rigidly fixed to at least a first electrode forming said one end adapted for piercing said tissue.

* * * * *